United States Patent
Xue et al.

(10) Patent No.: US 7,509,159 B2
(45) Date of Patent: Mar. 24, 2009

(54) METHOD AND APPARATUS FOR DETECTING CARDIAC REPOLARIZATION ABNORMALITY

(75) Inventors: Joel Q. Xue, Germantown, WI (US); G. Ian Rowlandson, Milwaukee, WI (US); David Albert, Oklahoma City, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 265 days.

(21) Appl. No.: 10/825,494

(22) Filed: Apr. 15, 2004

(65) Prior Publication Data

US 2005/0234357 A1 Oct. 20, 2005

(51) Int. Cl.
*A61B 5/04* (2006.01)
*A61B 5/02* (2006.01)

(52) U.S. Cl. .................. 600/513; 600/483; 600/517

(58) Field of Classification Search .............. 600/483, 600/509, 513, 515, 517, 518; 607/3
See application file for complete search history.

(56) References Cited

U.S. PATENT DOCUMENTS

| | | | |
|---|---|---|---|
| 3,554,187 A | 1/1971 | Glassner et al. | |
| 3,638,066 A | * 1/1972 | Paine et al. | 315/383 |
| 3,658,055 A | 4/1972 | Abe et al. | |
| 3,759,248 A | 9/1973 | Valiquette | |
| 3,821,948 A | 7/1974 | King | |
| 3,902,479 A | 9/1975 | Chaumet | |
| 3,952,731 A | 4/1976 | Worstencroft | |
| 4,124,894 A | 11/1978 | Vick et al. | |
| 4,136,690 A | 1/1979 | Anderson et al. | |
| 4,170,992 A | 10/1979 | Dillman | |
| 4,181,135 A | 1/1980 | Andresen et al. | |
| 4,202,340 A | 5/1980 | Langer et al. | |
| 4,316,249 A | 2/1982 | Gallant et al. | |
| 4,417,306 A | 11/1983 | Citron et al. | |
| 4,422,459 A | 12/1983 | Simson | |
| 4,432,375 A | 2/1984 | Angel et al. | |

(Continued)

FOREIGN PATENT DOCUMENTS

| | | |
|---|---|---|
| EP | 0080821 | 6/1983 |
| GB | 2070871 | 9/1981 |
| WO | WO81/02832 | 10/1981 |

OTHER PUBLICATIONS

Speranza et al., 'Beat-to-beat measurement and analysis of the R-T interval in 24 h ECG Holter recordings,' Med and Biol Eng & Comput, 1993, 31, pp. 487-494.

(Continued)

*Primary Examiner*—Carl H Layno
*Assistant Examiner*—Natasha N Patel
(74) *Attorney, Agent, or Firm*—Andrus, Sceales, Starke & Sawall, LLP

(57) ABSTRACT

Method and apparatus for detecting cardiac repolarization abnormality using at least one electrocardiogram signal. The at least one electrocardiogram signal can be obtained from any number of continuous or non-continuous windows. The method can include deriving a total quantity of representative beats of the at least one electrocardiogram signal. At least one morphology shape descriptor can be used to determine a total quantity of values representing the total quantity of representative beats. Data corresponding to at least some of the total quantity of values can be used to assess cardiac repolarization abnormality.

19 Claims, 4 Drawing Sheets

U.S. PATENT DOCUMENTS

| | | | |
|---|---|---|---|
| 4,457,315 | A | 7/1984 | Bennish |
| 4,458,691 | A | 7/1984 | Netravali |
| 4,458,692 | A | 7/1984 | Simson |
| 4,475,558 | A | 10/1984 | Brock |
| 4,492,235 | A | 1/1985 | Sitrick |
| 4,519,395 | A | 5/1985 | Hrushesky |
| 4,531,527 | A * | 7/1985 | Reinhold et al. ............ 600/509 |
| 4,583,553 | A | 4/1986 | Shah et al. |
| 4,589,420 | A | 5/1986 | Adams et al. |
| 4,603,703 | A | 8/1986 | McGill et al. |
| 4,616,659 | A | 10/1986 | Prezas et al. |
| 4,665,485 | A | 5/1987 | Lundy et al. |
| 4,679,144 | A | 7/1987 | Cox et al. |
| 4,680,708 | A | 7/1987 | Ambos et al. |
| 4,732,157 | A | 3/1988 | Kaplan et al. |
| 4,796,638 | A | 1/1989 | Sasaki |
| 4,802,491 | A * | 2/1989 | Cohen et al. ............... 600/515 |
| 4,832,038 | A | 5/1989 | Arai et al. |
| 4,854,327 | A | 8/1989 | Kunig |
| 4,860,762 | A | 8/1989 | Heumann et al. |
| 4,896,677 | A | 1/1990 | Kaneko et al. |
| 4,924,875 | A | 5/1990 | Chamoun |
| 4,928,690 | A | 5/1990 | Heilman et al. |
| 4,938,228 | A | 7/1990 | Righter et al. |
| 4,951,680 | A | 8/1990 | Kirk et al. |
| 4,955,382 | A | 9/1990 | Franz et al. |
| 4,958,641 | A | 9/1990 | Digby et al. |
| 4,972,834 | A | 11/1990 | Begemann et al. |
| 4,974,162 | A | 11/1990 | Siegel et al. |
| 4,974,598 | A | 12/1990 | John |
| 4,977,899 | A | 12/1990 | Digby et al. |
| 4,979,510 | A | 12/1990 | Franz et al. |
| 4,989,610 | A | 2/1991 | Patton et al. |
| 5,000,189 | A | 3/1991 | Throne et al. |
| 5,010,888 | A | 4/1991 | Jadvar et al. |
| 5,020,540 | A | 6/1991 | Chamoun |
| 5,025,795 | A | 6/1991 | Kunig |
| 5,042,497 | A | 8/1991 | Shapland |
| 5,092,341 | A | 3/1992 | Kelen |
| 5,109,862 | A | 5/1992 | Kelen et al. |
| 5,117,833 | A | 6/1992 | Albert et al. |
| 5,117,834 | A | 6/1992 | Kroll et al. |
| 5,148,812 | A | 9/1992 | Verrier et al. |
| 5,188,116 | A | 2/1993 | Pommrehn et al. |
| 5,201,321 | A | 4/1993 | Fulton |
| 5,215,098 | A * | 6/1993 | Steinhaus et al. ........... 600/515 |
| 5,234,404 | A | 8/1993 | Tuttle et al. |
| 5,253,650 | A | 10/1993 | Wada |
| 5,265,617 | A | 11/1993 | Verrier et al. |
| 5,277,190 | A | 1/1994 | Moulton |
| 5,323,783 | A | 6/1994 | Henkin et al. |
| 5,343,870 | A | 9/1994 | Gallant et al. |
| 5,423,878 | A | 6/1995 | Franz |
| 5,437,285 | A | 8/1995 | Verrier et al. |
| 5,514,164 | A * | 5/1996 | Mann et al. .................... 607/25 |
| 5,560,370 | A | 10/1996 | Verrier et al. |
| 5,570,696 | A | 11/1996 | Arnold et al. |
| 5,713,367 | A * | 2/1998 | Arnold et al. ............... 600/517 |
| 5,819,741 | A | 10/1998 | Karlsson et al. |
| 5,921,940 | A | 7/1999 | Verrier et al. |
| 5,935,082 | A | 8/1999 | Albrecht et al. |
| 6,047,206 | A * | 4/2000 | Albrecht et al. ............ 600/509 |
| 6,169,919 | B1 | 1/2001 | Nearing et al. |
| 6,438,409 | B1 * | 8/2002 | Malik et al. ................. 600/512 |
| 6,453,191 | B2 | 9/2002 | Krishnamachari |
| 6,571,122 | B2 * | 5/2003 | Schroeppel et al. ......... 600/515 |
| 6,656,126 | B2 | 12/2003 | Starobin et al. |
| 6,668,189 | B2 | 12/2003 | Kaiser et al. |
| 6,847,840 | B2 * | 1/2005 | DePasquale et al. ........ 600/516 |
| 6,983,183 | B2 * | 1/2006 | Thiagarajan et al. ........ 600/509 |
| 7,069,069 | B2 * | 6/2006 | Fishler et al. ............... 600/513 |

OTHER PUBLICATIONS

Narayanaswamy et al., 'Selective beat signal averaging and spectral analysis of beat intervals to determine the mechanisms of premature ventricular contractions,' University of Oklahoma Health Sciences Center, May 1993, pp. 81-84.

Laks et al., 'ECG computer program developed for a retrospective and prospective study of the Pardee T wave,' Department of Medicine, UCLA School of Medicine, Harbor-UCLA Medical Center, Torrence, CA, 1992, pp. 365-368.

Makarov et al., 'Holter monitoring in the long QT syndrome of children and adolescents,' Cor Vasa, 1990, 32(6), pp. 474-483.

Navarro-Lopez et al., 'Isolated T wave alternans elicited by hypocalcemia in dogs,' Electrocardiology, 1978, 11(2), pp. 103-108.

Little et al., 'Torsade de Pointes and T-U wave alternans associated with arsenic poisoning,' Pace, 1990, 13, pp. 164-170.

Weintraub et al., 'The congenital long QT syndromes in childhood,' Journal of the American College of Cardiology, Sep. 1990, 16(3), pp. 674-680.

Bibler et al., 'Recurrent ventricular tachycardia due to pentamidine-induced cardiotoxicity,' Chest, Dec. 1988, 94(6), pp. 1303-1306.

Ahnve et al., 'Circadian variations in cardiovascular parameters during sleep deprivation, A noninvasive study of young healthy men,' European Journal of Applied Physiology, 1981, 46, pp. 9-19.

Surawicz, 'ST-segment, T-wave, and U-wave changes during myocardial ischmeia and after myocardial infarction,' Canadian Journal of Cardiology, Supplement A, Jul. 1986, pp. 71A-84A.

Stroobandt et al., 'Simultaneous recording of atrial and ventricular monophasic action potentials: monophasic action potential duration during atrial pacing, ventricular pacing, and ventricular fibrillation,' Pace, Jul.-Aug. 1985, 8, pp. 502-511.

Sharma et al., 'Romano-Ward prolonged QT syndrome with intermittant T wave alternans and atrioventricular block,' American Heart Journal, 1981, pp. 500-501.

Navarro-Lopez et al., 'Isolated T wave alternans,' American Heart Journal, 1978, pp. 369-374.

Mitsutake et al., 'Usefulness of the Valsalva Maneuver in management of the long QT syndrome,' Circulation, 1981, 63(5), pp. 1029-1035.

Nearing et al., 'Personal computer system for tracking cardiac vulnerability by complex demodulation of the T wave,' American Physiological Society, 1993, pp. 2606-2612.

Joyal et al., 'ST-segment alternans during percutaneous transluminal coronary angioplasty,' Division of Cardiology, Department of Medicine, University of Florida and the Veterans Administration Medical Center, Jun. 1984, pp. 915-916.

Schwartz et al., 'Electrical alternation of the T-wave: clinical and experimental evidence of its relationship with the sympathetic nervous system and with the long Q-T syndrome,' American Heart Journal, Jan. 1975, 89(1), pp. 45-50.

Schwartz, 'Idiopathic long QT syndrome: progress and questions,' American Heart Journal, Feb. 1985, 109(2), pp. 399-411.

Verrier et al., 'Electrophysiologic basis for T wave alternans as an index of vulnerability fibrillation,' Journal of Cardiovascular Electrophysiology, May 1994, 5(5), pp. 445-461.

Verrier et al., 'Behavioral states and sudden cardiac death,' Pace, Sep. 1992, 15, pp. 1387-1393.

Turitto et al., 'Alternans of the ST segment in variant angina,' Chest, Mar. 1988, 93(3), pp. 587-591.

Ring et al., 'Exercise-induced ST segment alternans,' American Heart Journal, May 1986, 111(5), pp. 1009-1011.

Wayne et al., 'Exercise-induced ST segment alternans,' Chest, May 1983, 83(5), pp. 824-825.

Verrier et al., 'Ambulatory electrocardiogram-based tracking of T wave alternans in postmyocardial infarction patients to assess risk of cardiac arrest or arrhythmic death,' Journal of Cardiovascular Electrophysiology, Jul. 2003, 14(7), pp. 705-711.

* cited by examiner $$A = USV^T = [u_1, u_2, \ldots, u_p] \begin{bmatrix} s_1 & 0 & \cdots & 0 \\ 0 & s_2 & \cdots & 0 \\ \vdots & \vdots & & \vdots \\ 0 & 0 & \cdots & s_p \end{bmatrix} [v_1, v_2, \ldots, v_p]^T$$

FIG. 4

METHOD AND APPARATUS FOR DETECTING CARDIAC REPOLARIZATION ABNORMALITY

BACKGROUND OF THE INVENTION

The present invention relates to methods and apparatus for detecting cardiac repolarization abnormality.

Cardiac repolarization abnormality can be indicative of heart disease. In some cases, such as long QT syndrome, sudden cardiac death can be the first visible sign of such disease. Accordingly, cardiac repolarization has been studied to find a correlation between an electrocardiogram signal and an underlying heart disease of a patient. Conventional cardiac repolarization analyses often focus on the QT interval and/or the polarity of the T-wave.

Unfortunately, the cardiac repolarization process is very complex and thus the resulting portions of the electrocardiogram signal can be difficult to analyze. For example, it can be difficult to determine whether a change in the T-wave is due to onset of heart disease, due to alternative placement on the patient of the surface electrodes used to obtain the electrocardiogram signal, and/or due to noise (e.g., muscle noise). Interval analyses are limited in the detection of such changes and their sources. Also, measurement error of T-wave offset can affect both the sensitivity and the specificity of a particular application.

BRIEF DESCRIPTION OF THE INVENTION

In one embodiment the invention can provide a method of detecting cardiac repolarization abnormality using at least one electrocardiogram signal. The method can include determining a total quantity of representative beats of the at least one electrocardiogram signal, using at least one morphology shape descriptor to determine a total quantity of values representing the total quantity of representative beats, and using data corresponding to at least some of the values of the total quantity of values to assess cardiac repolarization abnormality.

BRIEF DESCRIPTION OF THE DRAWINGS

FIG. 4 illustrates a decomposition of a matrix data using a principal component analysis.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and software components or modules that, for purposes of discussion, may be illustrated and described as if the majority of the components were implemented solely in software. However, one of ordinary skill in the art, and based on a reading of this detailed description, would recognize that, in at least one embodiment, the software based aspects of the invention may be implemented in hardware. As such, it should be noted that a plurality of hardware and software based devices, as well as a plurality of different structural components may be utilized to implement the invention.

Figure 1:
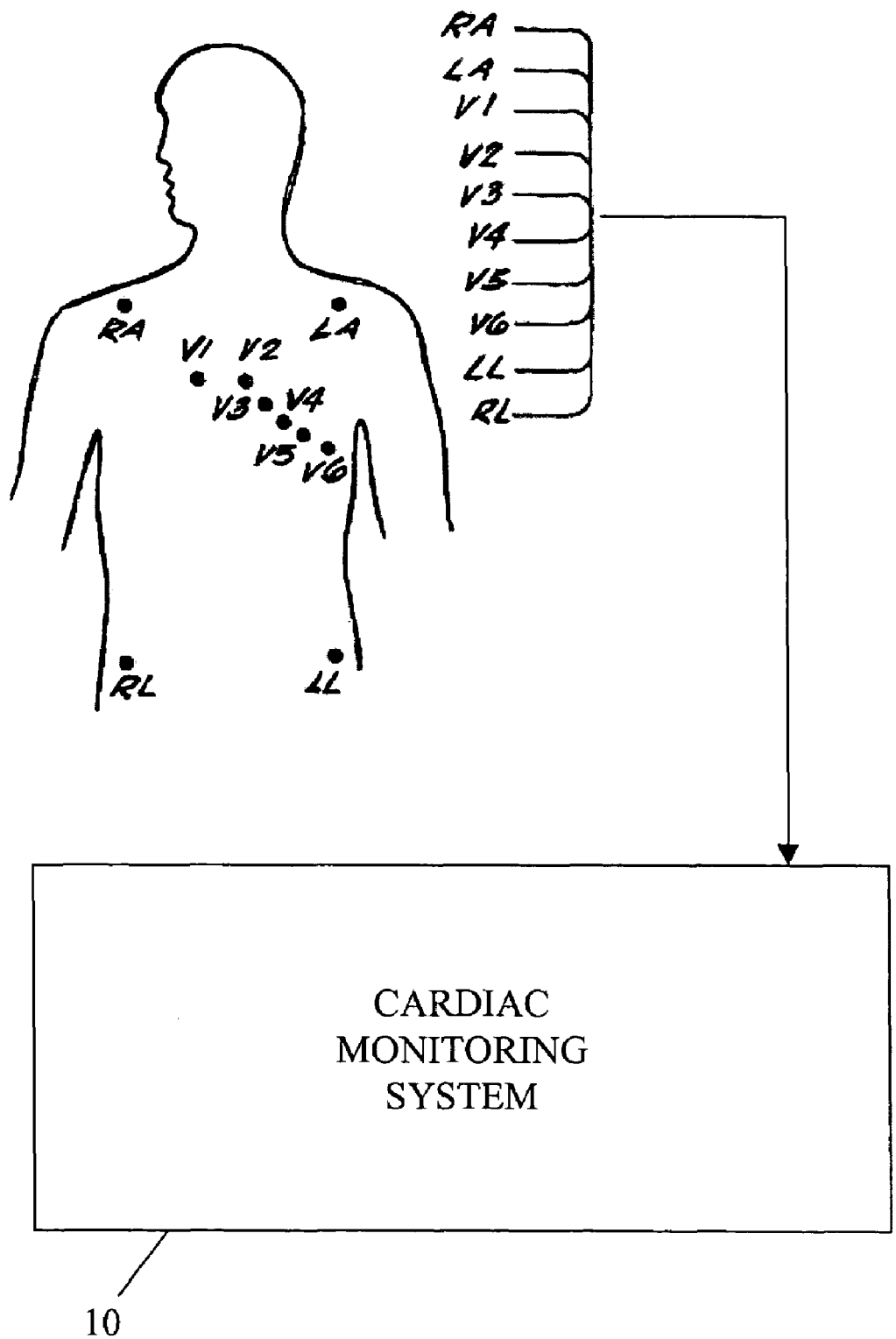
FIG. 1 is a schematic diagram illustrating a cardiac monitoring system according to the invention.

FIG. 1 illustrates a cardiac monitoring system 10 according to some embodiments of the invention. The cardiac monitoring system 10 can acquire electrocardiogram (ECG) data, can process the acquired ECG data to assess cardiac repolarization abnormalities, and can output data to a suitable output device (e.g., a display, a printer, and the like).

The cardiac monitoring system 10 can acquire ECG data using a data acquisition module. It should be understood that ECG data can be acquired from other sources (e.g., from storage in a memory device or a hospital information system). The data acquisition module can be coupled to a patient by an array of sensors or transducers which may include, for example, electrodes coupled to the patient for obtaining an ECG signal. In the illustrated embodiment, the electrodes can include a right arm electrode RA; a left arm electrode LA; chest electrodes V1, V2, V3, V4, V5 and V6; a right leg electrode RL; and a left electrode leg LL for acquiring a standard twelve-lead, ten-electrode ECG. In other embodiments, alternative configurations of sensors or transducers (e.g., less than ten electrodes, or with extra leads such is utilized in a fifteen lead system) can be used to acquire a standard or non-standard ECG signal.

Figure 2:
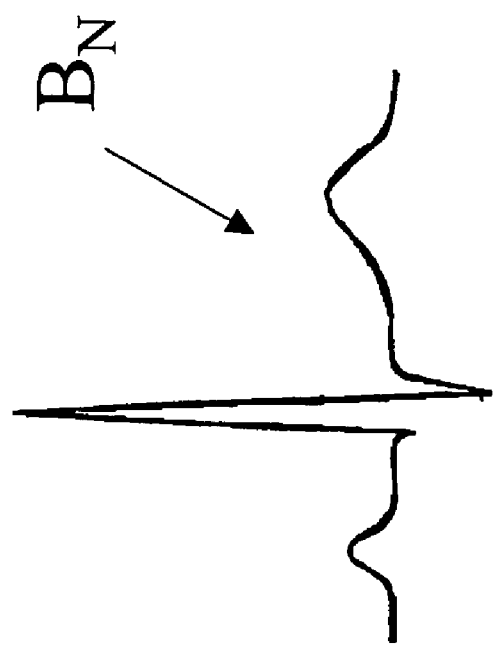
FIG. 2 illustrates an electrocardiogram signal.
Figure 2:
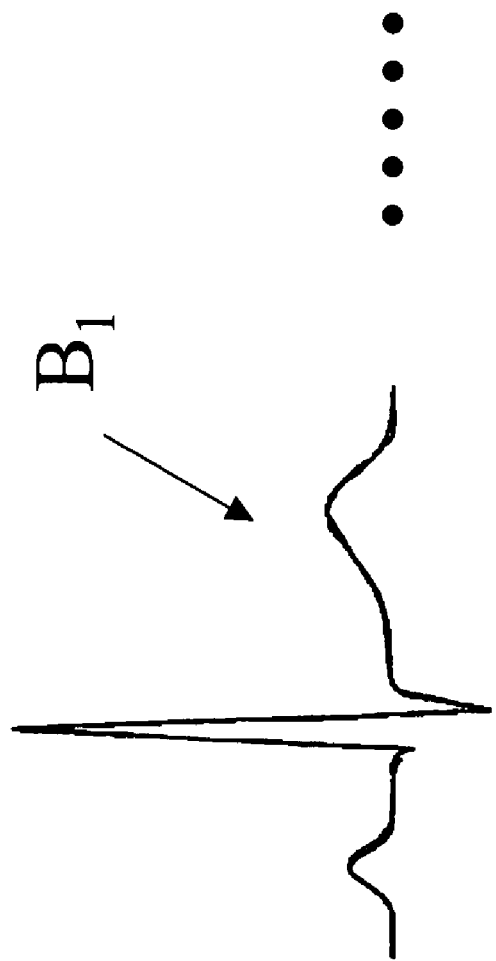

A representative ECG signal is schematically illustrated in FIG. 2. The ECG signal can include N beats including beat-one $B_1$ through beat-N $B_N$ where N is a value greater than one. The ECG signal can include continuous and/or non-continuous beats B.

The data acquisition module can include filtering and digitization components for producing digitized ECG data representing the ECG signal. In some embodiments, the ECG data can be filtered using low pass and baseline wander removal filters to remove high frequency noise and low frequency artifacts. The ECG data can, in some embodiments, be filtered by removing arrhythmic beats from the ECG data and by eliminating noisy beats from the ECG data.

Figure 3:
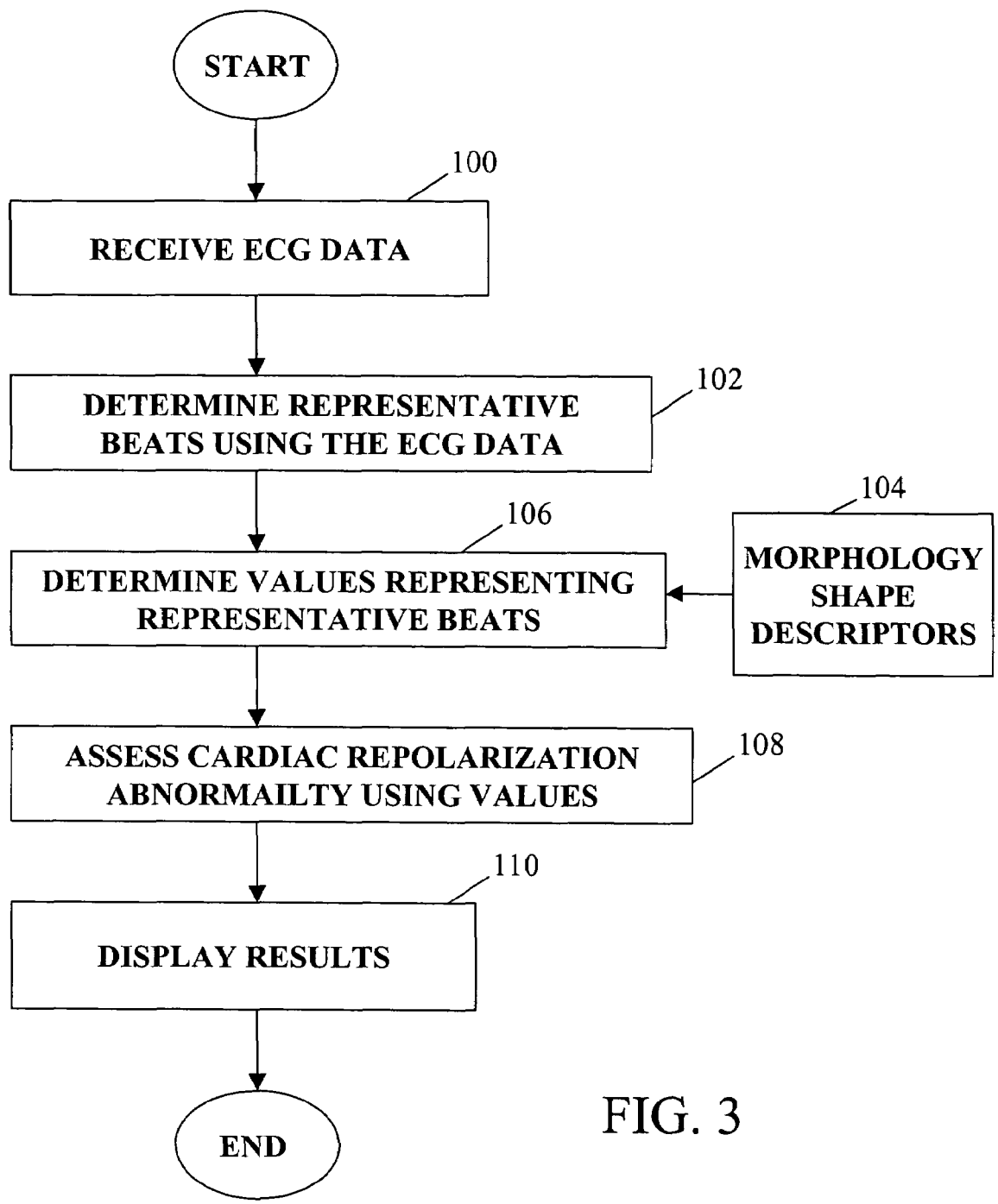
FIG. 3 is a flow chart illustrating one embodiment of a method of the invention.

The cardiac monitoring system 10 can include a processor and a memory associated with the processor. The processor can execute a software program stored in the memory to perform a method of the invention as illustrated in FIG. 3. FIG. 3 is a flow chart of a method of the invention used to detect cardiac repolarization abnormality using at least one ECG signal. Although the cardiac monitoring system 10 is described herein as including a single processor that executes a single software program, it should be understood that the system can include multiple processors, memories, and/or software programs. Further, the method of the invention illustrated in FIG. 3 can be performed manually or using other systems.

As shown in FIG. 3, the processor can receive (at 100) ECG data representing an ECG signal. The acquired ECG data can be received (e.g., from a patient in real-time via the data acquisition module, from storage in a memory device, remotely through a network) and can be processed as necessary. The ECG data can represent continuous and/or non-continuous beats of the ECG signal. For example, in some embodiments, the ECG signal can be obtained during a single time window (e.g., a ten to twenty second time window), while in other embodiments, the ECG signal can be obtained during multiple time windows. Further, the ECG data can represent one or more ECG signals (e.g., a first ECG signal obtained a first day, a second ECG signal obtained a second day, and so on).

The processor can determine (at 102) a quantity of representative beats using the ECG data. To facilitate determination of the representative beats, the ECG data, or a portion thereof, can be parsed into a plurality of data sets. Each data set can represent a portion of a respective beat B of the ECG signal (e.g., the T-wave portion of a respective beat B of the ECG signal), a portion of a respective odd or even median beat of the ECG signal, a portion of a respective odd or even mean beat of the ECG signal, a portion of each lead of the ECG signal, and the like. The parsed data sets can be saved in an array (e.g., a waveform array). In other embodiments, the ECG data can be saved in a single data set, or alternatively, saved in multiple data sets.

As shown in FIG. 3, the processor can use at least one morphology shape descriptor 104 to determine (at 106) a quantity of values representing the representative beats. The morphology shape descriptor can include many different designs. A number of example designs of morphology shape descriptors are described below.

In one embodiment, a morphology shape descriptor can be designed to describe a representative beat using at least one morphology feature of a curve formed by a data set corresponding to the representative beat. In some embodiments, the data set can directly correspond to the representative beat. In other embodiments, the data set can indirectly correspond to the representative beat (e.g., the data set can correspond to a first derivative of the representative beat, an integration of the representative beat, and the like). The morphology feature can include, for example:

a maximum morphology feature (e.g., a maximum value of a data set corresponding to a representative beat);

a minimum morphology feature (e.g., a minimum value of a data set corresponding to a representative beat);

an area morphology feature (e.g., an area between a curve formed by a data set corresponding to a representative beat and a baseline established by a minimum value of the data set, an area between a curve formed by a data set corresponding to a representative beat and a baseline established by a maximum value of the data set and a point of the data set representing a maximum up-slope of the curve, an area between a curve formed by a data set corresponding to a representative beat and a baseline established by a minimum value of the data set and a point of the data set representing a maximum down-slope of the curve, an area between a curve formed by a data set corresponding to a representative beat and a baseline established by a point of the data set representing a maximum up-slope of the curve and a point of the data set representing a maximum down-slope of the curve, and the like);

an amplitude morphology feature (e.g., an amplitude of a point representing a maximum up-slope of a curve formed by a data set corresponding to the representative beat, an amplitude of a point representing a maximum down-slope of a curve formed by a data set corresponding to a representative beat, a ST-wave amplitude, a T-wave peak amplitude, a T-wave valley amplitude, a U-wave peak amplitude, and the like);

a slope morphology feature (e.g., a maximum up-slope of a curve formed by a data set corresponding to a representative beat, a maximum down-slope of a curve formed by a data set corresponding to a representative beat, a maximum T-wave up-slope, a maximum T-wave down slope, and the like);

a time interval morphology feature (e.g., a time interval between a maximum value and a minimum value of a data set corresponding to a representative beat);

a ratio morphology feature (e.g., a ST:T ratio); and any combination thereof.

In some embodiments, values generated using the morphology features can be placed in a matrix for further processing. In one embodiment, a matrix can be generated that includes rows that represent the leads of an ECG signal and columns that represent morphology features of the representative beats corresponding to each lead.

In another embodiment, a morphology shape descriptor can be designed to describe a representative beat using results of a principal component analysis (PCA) performed on a matrix of data A (FIG. 4) having data corresponding to one or more representative beats (e.g., beats representative of twelve leads of an ECG signal). In some embodiments, the matrix of data A can include values determined using at least some of the above noted morphology features.

PCA involves a multivariate mathematical procedure known as an eigen analysis which rotates the data to maximize the explained variance of the matrix of data A (i.e., a set of correlated variables are transformed into a set of uncorrelated variables which are ordered by reducing variability, the uncorrelated variables being linear combinations of the original variables). The PCA decomposes the matrix of data A into three matrices as illustrated in FIG. 4. The three matrices include a matrix U, a matrix S, and a matrix V. The matrix U includes the principal component vectors (e.g., the first principal component vector $u_1$, the second principal component vector $u_2$, . . . , the pth principal component vector $u_p$). The principal component vectors are also known as eigen vectors. In the illustrated embodiment, the first principal component vector $u_1$ represents the most dominant variance vector, the second principal component vector $u_2$ represents the second most dominant variance vector, and so on. The S Matrix includes the principal components (e.g., the first principal component $S_1$, the second principal component $S_2$, . . . , the pth principal component $S_p$). The first principal component $S_1$ accounts for as much of the variability in the data as possible, and each succeeding principal component S accounts for as much of the remaining variability as possible. The matrix V is generally known as the parameter matrix. The matrix V is raised to a power of T.

In one embodiment, the first principal component vector $u_1$, the second principal component vector $u_2$, and the third principal component vector $u_3$ can be utilized as a dipolar shape descriptor, and the fourth principal component vector $u_4$, the fifth principal component vector $u_5$, and the sixth principal component vector $u_6$ can be utilized as a non-dipolar shape descriptor. In other embodiments, the results of the PCA can be used alternatively to describe the representative beats.

In another embodiment, a morphology shape descriptor can be designed to describe a representative beat using results of a wavelet analysis. A wavelet analysis is a transform that provides a time-frequency representation of a set of data. In one embodiment, a discrete wavelet analysis is performed on the first principal component vector $u_1$, the second principal component vector $u_2$, the third principal component vector $u_3$, the fourth principal component vector $u_4$, and the fifth principal component vector $u_5$, which were obtained by performing a PCA on multiple leads of a ST-T portion of a representative beat. A feature set can then be extracted from the first, second, and third levels of discrete wavelet transform coefficients for the principal component vectors. This step is a further generalization or feature reduction from both the PCA and wavelet analysis.

In another embodiment, a morphology shape descriptor can be designed to describe a representative beat using a mathematical modeling function. The mathematical modeling function can be utilized to determine values representing a mathematical model of a curve formed by a data set corresponding to the representative beat. The mathematical modeling function may include at least one of a Gaussian function model (e.g., a two-sided Gaussian function model), a power of Cosine function model, a bell function model, and any combination thereof.

In another embodiment, a morphology shape descriptor can be designed to describe a representative beat using results from a direct waveform extraction, or the cross-correlation with a template waveform, which can become auto-correlation if the template is the waveform itself. One example of a direct waveform extraction can include a neural net trained to generate various outputs when the neural net recognizes abnormalities in a data set corresponding to a representative beat. In one embodiment, the direct waveform extraction can be from a ST-T segment of either an original lead or PCA vectors.

In another embodiment, a morphology shape descriptor can be designed to describe a representative beat using standard electrocardiographic measurements and feature extraction. One example of a feature extraction can include whether the representative beat includes a concave or convex ST-T wave.

The quantity of values determined for each representative beat using the morphology shape descriptors 104 can vary. As shown in FIG. 3, the processor can use the values representing the representative beat to quantitatively assess (at 108) cardiac repolarization abnormality. In some embodiments, a single ECG analysis can be performed. In other embodiments, a serial ECG analysis or comparison can be performed. Quantitative assessment of cardiac repolarization abnormality allows for trending, which can lead to a better understanding of how heart disease affects a patient's ECG signal. This understanding can then be utilized to better predict sudden cardiac death and other cardiac related diseases. For example, as numerous ECG signals are analyzed, threshold levels can be established for the various values representing the representative beats. When one or more threshold levels are exceeded, the patient may be a candidate for further testing.

In some embodiments, the values determined using the morphology shape descriptors can be compared with a template to determine levels and/or patterns of variation therefrom. In some embodiments, the template can be generated using one or more of the values with the combination of the above morphology descriptors. In other embodiments, the template can be formed based on preexisting data.

As an illustrative example of using a template, a first representative beat may generate a value of five units when analyzing the representative beat with a particular morphology shape descriptor, a second representative beat may generate a corresponding value of six units, a third representative beat may generate a corresponding value of four units, a fourth representative beat may generate a corresponding value of ten units, and so on. The first, second, third, and fourth representative beats may represent beats from a single ECG signal or beats from four separate ECG signals (e.g., ECG signals periodically taken over a year span). If the template is derived using a single value, the template can have a value of five units. In other embodiment, the template can be more complex. When the second representative beat is compared to the template, an absolute difference of one unit results, when the third representative beat is compared to the template, an absolute difference of one unit results, and when the fourth representative beat is compared to the template, an absolute difference of five units results. Each of these variations can then be compared to a threshold value to determine if the threshold is exceeded. If the threshold value is three units of variance, then the first and second representative beats do not exceed the threshold but the third representative beat does exceed the threshold. This out-of-range variation can be cause for further testing of the patient. In some embodiments, a determination that further testing is necessary may depend on the type of out-of-range variation and/or the existence of other out of range variations.

In some embodiments, the template can be adaptively adjusted based on the variation from the template during a time series analysis. Many different techniques can be used to adjust and refine the templates. For example, in one embodiment, the template is adjusted based on a small percentage of the variation resulting from each comparison. Such adjustment can be especially beneficial in long-term trending studies where other variables may be changing that affect the values being compared with the template, for example, the changing due to heart rate and activity status (e.g., sleep versus wake-up).

In some embodiments, the values can be normalized prior to comparison to the template. Such normalization may be especially necessary, for example, if the values represent beats of ECG signals, which were not obtained using the same set of electrodes. ECGs obtained from a patient can vary based on placement of electrodes on the patient. Many normalization techniques can be used to normalize the values. For example, in one embodiment, the values can be normalized based on the QRS deflection of the representative beat.

In some embodiments, the method of the invention can allow for the use of patients as their own controls in pharmaceutical testing. Use of patients as their own controls can eliminate the need for separate control groups. For example, in one embodiment, at least one ECG signal is obtained prior to delivery of the pharmaceutical drug to the patient, and at least one ECG signal is obtained during and/or after delivery of the drug to the patient. The sets of ECG data can then be statistically analyzed individually and then relative to each other to determine if a statistically significant change exists. In some embodiments, normal day-to-day variability versus statistically significant change can be measured via cluster analysis. In other embodiments, alternative statistical analyses can be utilized. Populations of patients can be studied and separated into separate groups based on these statistical analyses.

In some embodiments, non-electrocardiogram correlates of cardiac repolarization can be utilized for purposes of further assessing cardiac repolarization abnormality. For example, in one embodiment, a patient can be tagged with measurements that do not change over time (e.g., genetic profiles). Populations of patients with similar cardiac disease can then be compared to determine if tag similarities exist, which may act as an indicator of oncoming cardiac disease. Further, in other embodiments, the patient can be tagged with measurements that do change over time (e.g., prevalence of disease, cardiac enzymes, blood pressure). As analysis reveals that the patient is developing cardiac disease, the tags can also be analyzed to determine if their values are also changing. Such analysis can lead to additional indicators or causes of the cardiac disease.

As shown in FIG. 3, the processor can display (at 110) the results of the method of the invention. The results can be displayed using any suitable output device (e.g., printer, display, and the like). In some embodiments, editing tools can be utilized to manipulate and further analyze the results.

Various aspects of the invention are set forth in the following claims.

What is claimed:

1. A method of detecting cardiac repolarization abnormality using at least one electrocardiogram signal, the method comprising:
    deriving a total quantity of representative beats of the at least one electrocardiogram signal taken from a patient ECG;
    using at least one morphology shape descriptor to determine a total quantity of values representing the total quantity of representative beats;
    generating a template using at least one value corresponding to at least one of the representative beats;
    comparing the template and at least one value corresponding to at least one other of the representative beats for a variation;
    comparing the variation to a threshold value, wherein the threshold value is derived from trending, further wherein trending includes a time serial analysis; and
    using data corresponding to at least some of the total quantity of values to assess cardiac repolarization abnormality in the patient.

2. A method as set forth in claim 1 wherein the total quantity of representative beats comprises at least one beat representative of each lead of the at least one electrocardiogram signal.

3. A method as set forth in claim 1 wherein a cardiac repolarization abnormality exists if a variation between the template and the at least one value corresponding to at least one other of the representative beats is greater than a threshold value.

4. A method as set forth in claim 3 and further comprising adaptively adjusting the threshold value based at least in part on a level of noise in the at least one electrocardiogram signal.

5. A method as set forth in claim 1 and further comprising altering the template based at least in part on the at least one value corresponding to the at least one other of the representative beats.

6. A method as set forth in claim 1 and further comprising normalizing at least some of the values of the total quantity of values.

7. A method as set forth in claim 1 wherein the at least one electrocardiogram signal comprises a first electrocardiogram signal representative of a first duration of time and a second electrocardiogram signal representative of a second duration of time, and wherein the first duration of time and the second duration of time are non-continuous.

8. A method as set forth in claim 1 and further comprising:
    administering a pharmaceutical drug to a patient;
    obtaining the at least one electrocardiogram signal from the patient, the at least one electrocardiogram signal comprising a first electrocardiogram signal comprising beats prior to the administration of the pharmaceutical drug and a second electrocardiogram signal comprising beats after the administration of the pharmaceutical drug; and
    determining a variation between values of the total quantity of values that correspond to the first electrocardiogram signal and values of the total quantity of values that correspond to the second electrocardiogram signal.

9. A method as set forth in claim 8 and further comprising statistically analyzing the variation.

10. A method as set forth in claim 1 and further comprising tagging at least one value of the total quantity of values with a marker.

11. A method as set forth in claim 10 wherein the marker is a measurement that does not change over time.

12. A method as set forth in claim 10 wherein the marker is a measurement that changes over time.

13. A method as set forth in claim 10 and further comprising using the marker as part of a discriminator of cardiac repolarization abnormality.

14. A method as set forth in claim 1 and further comprising displaying data corresponding to the at least one electrocardiogram signal.

15. A method of detecting cardiac repolarization abnormality using at least one electrocardiogram signal, the method comprising:
    deriving a total quantity of representative beats of the at least one electrocardiogram signal taken from a patient ECG;
    using at least one morphology shape descriptor to determine a total quantity of values representing the total quantity of representative beats;
    generating a template using at least one value corresponding to at least one of the representative beats;
    comparing the template and at least one value corresponding to at least one other of the representative beats for a variation; and
    comparing the variation to a threshold value, wherein the threshold value is derived from trending, further wherein trending includes a time serial analysis.

16. A method as set forth in claim 15 wherein the total quantity of representative beats comprises at least one beat representative of each lead of the at least one electrocardiogram signal.

17. A method as set forth in claim 15 wherein the at least one electrocardiogram signal comprises a first electrocardiogram signal representative of a first duration of time and a second electrocardiogram signal representative of a second duration of time, and wherein the first duration of time and the second duration of time are non-continuous.

18. A method as set forth in claim 15 and further comprising:
    administering a pharmaceutical drug to a patient;
    obtaining the at least one electrocardiogram signal from the patient, the at least one electrocardiogram signal comprising a first electrocardiogram signal comprising beats prior to the administration of the pharmaceutical drug and a second electrocardiogram signal comprising beats after the administration of the pharmaceutical drug; and
    determining a variation between values of the total quantity of values that correspond to the first electrocardiogram signal and values of the total quantity of values that correspond to the second electrocardiogram signal.

19. A device for detecting cardiac repolarization abnormality using at least one electrocardiogram signal, the device comprising:
    means for generating a total quantity of representative beats of the at least one electrocardiogram signal taken from a patient ECG;

means for using at least one morphology shape descriptor to determine a total quantity of values representing the total quantity of representative beats means for;
generating a template using at least one value corresponding to at least one of the representative beats means for;
comparing the template and at least one value corresponding to at least one other of the representative beats for a variation means for;
comparing the variation to a threshold value, wherein the threshold value is derived from trending, further wherein trending includes a time serial analysis; and
means for using data corresponding to at least some of the total quantity of values to assess cardiac repolarization abnormality in the patient.

* * * * *